United States Patent [19]

Lalonde

[11] 4,366,245

[45] Dec. 28, 1982

[54] METHOD FOR THE ISOLATION OF SYMBIOTIC MICROORGANISMS FROM HOST PLANTS USING AN OSMIUM TETRAOXIDE FIXATIVE

[76] Inventor: Maurice Lalonde, c/o The Charles F. Kettering Research Laboratory, 150 E. South College St., Yellow Springs, Ohio 45387

[21] Appl. No.: 212,395

[22] Filed: Dec. 3, 1980

[51] Int. Cl.$^3$ .............................................. C12Q 1/24
[52] U.S. Cl. ..................................... 435/30; 435/803
[58] Field of Search ................... 435/4, 29, 30, 31, 34, 435/36, 37, 38, 39, 40, 800, 803

[56] References Cited

PUBLICATIONS

Dale Callaham et al., Science, vol. 199, pp. 899–902 (1978).
"The Isolation and Cultivation of Actinomycetous Root Nodule Endophytes", In Symbiotic Nitrogen Fixation in the Management of Temperate Forests, Oregon St. University, proceedings of Workshop held, Apr. 2–5, 1979, pp. 38–56, Baker et al.
Baker et al., "Separation of Actinomycete Nodule Endophytes from Crushed Nodules Suspensions by Sephadex Fractionation," *Bot. Goz.*, vol. 140 (suppl.), 549–551 (1979).

*Primary Examiner*—Robert J. Warden
*Attorney, Agent, or Firm*—Biebel, French & Nauman

[57] ABSTRACT

Symbiotic microorganisms such as nitrogen fixing bacteria and phosphorus-providing fungi are isolated from nodules and mycorrhiza on the roots of host plants by sterilizing the surface and subsurface areas of root tissue with an aqueous solution of a fixative containing osmium tetraoxide. The osmium tetraoxide is highly soluble in water, and volatilizes at room temperature to form a vapor which penetrates subsurface air pockets in root tissues to kill contaminating microorganisms. The osmium tetraoxide also provides a visual indicator of its progress through plant tissue by a progressive darkening of such tissue from the surface of root samples toward their centers. In this manner, the sterilization can be halted before the centrally located causitive bacteria is destroyed.

7 Claims, No Drawings

METHOD FOR THE ISOLATION OF SYMBIOTIC MICROORGANISMS FROM HOST PLANTS USING AN OSMIUM TETRAOXIDE FIXATIVE

BACKGROUND OF THE INVENTION

This invention relates to a process for the isolation of endosymbiont nitrogen-fixing bacteria and phosphorous-providing fungi in the roots of plants, and more particularly to an improved surface sterilization process for such roots to isolate the bacteria and fungi.

Nitrogen and phosphorus are essential mineral nutrients for plants. A shortage or lack of either nutrient in soils will adversely affect plant growth. Heretofore, nitrogen and phosphorus have been supplied to crops and other bromass producing plants by the addition of fertilizers to the soil. However, increasing costs of producing such fertilizers have led to searches for alternative methods of supplying these mineral nutrients to growing plants.

It is known that nitrogen-fixing root nodules occur on both leguminous and non-leguminous plants. Members of the legume family whose roots are infected by the soil bacterium Rhizobium are the primary source of nitrogen fixation in agricultural systems. Some non-leguminous angiosperms form root nodules when invaded by soil actimomycetes bacteria which also enable fixation of atmosphere nitrogen by these plants. Additionally, it is known that certan fungi produce ectomycorrhizal and endomycorrhizal growths on plant root systems which can provide phosphorus to several plant species including some which are agriculturally important.

Presently, the successful growth of nitrogen-fixing bacteria or phosphorus-providing fungi on a particular host plant depends on the presence of an endogenous population of such bacteria or fungi in the soil in which the plant is growing. When planted in soils having a low concentration of mineral nutrients, the absence of early and effective growth of root nodules and/or mycorrhiza delays the establishment and growth of seedlings and may even result in their complete failure. Previous methods of inoculating seedlings with suspensions of ground-up nodules or applying soil suspensions taken from where host plants were growing gave unpredictable and variable results because such suspensions contained a wide range of soil microorganisms as well as complex products derived from broken plant tissues.

Clearly, the need exists for techniques which will enable the isolation and cultivation of the causative bacteria and fungi which can then be used to inoculate seeds and/or seedlings. While isolation and identification of Rhizobium bacteria from legume root nodules have been known for sometime, only recently have successful isolation techniques been developed for certain non-leguminous plants. See, Callaham et al., *Science*, volume 199, pp. 899-902 (1978). Such techniques include surface sterilization of root nodules using sodium hypochlorite or mercury chloride solutions followed by microdissection and enzymetic digestion or suspension and dilution of the host tissues. Other reported techniques for isolating such bacteria from root nodules include Sephadex and sucrose density fractionation.

However, these techniques have not proved to be entirely satisfactory. Not only are they time consuming and technically complex, they exhibit a very high failure rate in successfully isolating the causative bacteria. Presently utilized surface sterilization techniques, designed to kill the wide variety of other soil microorganisms found on root nodules while leaving unaffected the causative bacteria and fungi, have not been successful. This is due to several factors. One factor is that air pockets and small pathways in the interior of such root nodules harbor a variety of microorganisms which the surface sterilant does not reach. When the root nodules are crushed or dissected, these microorganisms are transferred along with the desired endophytes to a cultivation medium, causing contamination of the medium. Another factor is that the surface sterilants heretofore used in many cases act so quickly on the root nodules and mycorrhizal growths that all of the desired microorganisms are killed along with the rest of the microorganisms.

Accordingly, the need exists in the art for an improved isolation technique for nitrogen-fixing bacteria and phosphorus-providing fungi which is both simple to perform and results in a high success rate in providing an isolated culture.

SUMMARY OF THE INVENTION

In accordance with the present invention, symbiotic microorganisms such as bacteria and fungi are isolated from nodules and mycorrhiza on the roots of host plants by first sterilizing the surface of the roots with an aqueous solution of a fixative containing osmium tetraoxide. The osmium tetraoxide is effective in killing microorganisms, is highly soluble in water, and volatilizes readily at room temperature to form a vapor. This volatility aids in allowing the osmium tetraoxide to penetrate subsurface air pockets in root tissue and kill contaminating microorganisms.

Moreover, because of the relatively large size of the osmium atom, and thus the osmium tetraoxide molecule, the molecule penetrates plant tissue very slowly as compared to prior art fixatives used as surface sterilants. Because of this slow penetration of root tissue, the sterilization of roots of sample plants can be controlled. That is, the osmium tetraoxide can be used to kill all surface and subsurface contaminating microorganisms and then be rinsed from the root sample before it has penetrated to the core of the sample. This permits the symbiotic bacteria and fungi of interest to survive and be isolated.

An additional advantage in the use of osmium tetraoxide in the practice of the invention is that as it contacts plant tissue, some of the tetraoxide compound reacts to form osmium hydroxide, a visually black precipitate. Thus, the optimum treatment time for root samples can be easily determined by a visual observation of the progressive darkening of the root tissue from its periphery toward its center. Once the osmium tetraoxide has penetrated sufficiently below the surface of the sample to kill all contaminating microorganisms, the sterilization can be stopped, based on visual observations, and the endophytic symbiotic bacteria and fungi can be recovered alive.

Once recovered, these symbiotic bacteria and fungi are then transferred to an appropriate growth medium where sufficient quantities may be grown for use as inoculants for other host plants. Such plants can be inoculated using known techniques such as applying an aqueous suspension of the symbiotic bacteria or fungi to host plant seeds or to the soil surrounding host plant seedlings. In this manner, the host plants are provided with sources of nitrogen and/or phosphorus from their symbiotic relationship with bacteria and/or fungi even in mineral-poor soils without the need for the application of expensive fertilizers.

Accordingly, it is an object of the present invention to provide an improved technique for isolating nitrogen-fixing bacteria and phosphorus-providing fungi from host plants which is both simple and has a high success rate in providing an isolated culture. This and other objects and advantages of the invention will be apparent from the following description and appended claims.

DESCRIPTION OF THE PREFERRED EMBODIMENTS

In accordance with the practice of the present invention, fresh root tissue samples containing nodules or mycorrhiza can be collected directly from field-grown and/or greenhouse-grown plants. The isolation technique of the present invention is useful in separating several types of both nitrogen-fixing bacteria and phosphorus-providing fungi.

For example, soil actinomycetes, such as various Frankia strains, which nodulate the root systems of nonleguminous angiosperms are known nitrogen-fixing endophytes. Rhizobium bacteria are also known to form root nodules and fix nitrogen in legumes. Several strains of phosphorous-providing fungus induced ecto-and endomycorrhizae also are known to exist in symbiosis with agriculturally important plants. All of these types of symbiotic microorganisms can be isolated using the technique of the present invention.

Root tissue samples containing the desired bacteria or fungi are collected and small pieces (i.e., 2–5 mm in length) are then immersed in a fixative solution containing osmium tetraoxide. Typically, the amount of osmium tetraoxide in solution can vary from 1–5%, by weight with 3% by weight being preferred. Lesser and greater strength solutions can be used, although the time need to fix effectively the contaminating surface and subsurface organisms in the tissue samples will need to be varied depending upon the concentration of the solution and the size and type of samples. The greater the concentration of osmium tetraoxide, the faster the sterilization proceeds. Generally, a 3% osmium tetraoxide in 0.05 M phosphate buffered saline solution having a pH of about 7.2 with 0.6% by weight calcium chloride has been found to be effective when contacted with tissue samples for from 30 seconds to 6 minutes. Tissues are fixed at room temperature.

Osmium tetraoxide is a highly potent fixative which is readily soluble in water and tends to volatilize at room temperature. Accordingly, it is the preferred fixative for the present process, although, other fixative materials could also be used if they had the same characteristics as osmium tetrooxide, including the ability to volatilize at room temperature. The vaporization of osmium tetraoxide aids in its penetration into subsurface air pockets to kill contaminating microorganisms. However, because of its toxic vapors, care should be taken when using it; good ventilation and a fume hood is recommended for handling solutions.

Another advantage in the use of osmium tetraoxide is that its optimum fixation time for tissue samples can be readily determined by a visual observation of the progressive darkening of the tissue samples from the periphery toward the center caused by the formation of osmium hydroxide. Since the object of the isolation technique is to preserve at least some of the desired bacteria or fungal strains alive, sample root tissue should be fixed only to the extent of killing surface and subsurface organisms. This technique works well with the endophytic bacteria and fungal strains and also works to isolate some ectomycorrhizal fungi because at least a portion of the desired species can be found in the interior of a tissue sample.

The sterilization procedure is terminated by removing the tissue samples from the osmium tetraoxide solution and rinsing them in sterile water. The rinsing procedure should be repeated one or more times to insure that all traces of fixative are washed away. The water-rinsed tissue samples are then immersed aseptically in a sterile solution containing an appropriate buffer solution such as a 0.05 M phosphate buffered saline (0.6% NaCl, pH=7.2) which also contains approximately 0.1% W/V of soluble polyvinylpyrrolidone. The use of polyvinylpyrrolidone in the buffer immobilizes phenols contained in some plant tissues.

After immersion for a few minutes in the buffer solution, the tissue samples are divided into several pieces (i.e., 2–6 pieces per sample) using an appropriate sterile tool such as a needle, razor blade, or scalpel. Each piece is then transferred aseptically to an appropriate sterile liquid or gelled growth medium. One growth medium which has been found to suitable for cultivation of numerous endophytes is a growth medium identified as Qmod by Lalonde and Calvert, "Production of Frankia Hyphae and Spores as an Infective Inoculant for Alnus Species," Symbiotic Nitrogen Fixation in the Management of Temperate Forests, Workshop held Apr. 2–5, 1979, Oregon State University, Corvallis, Oreg. This Qmod growth medium has the following constituents:

|  | per liter |
|---|---|
| $K_2HPO_4$ | 300 mg |
| $NaH_2PO_4$ | 200 mg |
| $MgSO_4.7H_2O$ | 200 mg |
| KCl | 200 mg |
| Yeast Extract (BBL) | 500 mg |
| Bacto-Peptone (DIFCO) | 5 g |
| Glucose | 10 g |
| Ferric Citrate (Citric Acid and Ferric Citrate, 1% sol.) | 1 ml |
| Minor Salts* | 1 ml |
| $H_2O$, Deionized to: | 1 l |
| adjust pH to 6.8–7.0 with NaOH or HCl | |
| then add, $CaCO_3$ | 100 mg |
| Lipid Supplement** | 0.5–50 mg |
| Agar, if used | 15 g |
| Mix thoroughly and pour 15 ml per tube, autoclave for 20 min. | |

*Minor Salts (g/liter): $H_3BO_3$, 1.5; $MnSO_4.7H_2O$, 0.8; $ZnSO_4.7H_2O$; 0.6; $CuSO_4.7H_2O$, 0.1; $(NH_4)_6Mo_7O_{24}.4H_2O$, 0.2; $CoSO_4.7H_2O$, 0.01.
**Lipid Supplement: dissolve 500 mg of L-α-lecithin (commercial grade from soybeans, 22% phosphatidyl choline, P-5638 from Sigma Chemical Co., St. Louis, MO) in 50 ml of absolute ethanol, and add 50 ml of distilled water.

The inoculated growth medium is then incubated at from 15°–27° C. for from several days to a few weeks until a sufficient growth of the isolated bacteria or fungus is observed. This bacteria or fungus can then be inoculated onto seeds or seedlings to infect them with the desired symbiotic nitrogen-fixing or phosphorus-providing culture. The success of the isolation technique of the present invention has been found to average more than 50%. That is, more than 50% of the pieces isolated by the technique, when cultured, produce pure cultures of the desired microbial isolate.

The following nonlimiting example is provided to illustrate the practice of the present invention.

EXAMPLE

Root nodule samples containing a Frankia strain of nitrogen-fixing soil actinomycetes were collected from an *Alnus serrulate* host plant growing in soil in a green house. The nodule samples were promptly treated in accordance with the practice of the present invention. The samples were immersed in a 3% solution of osmium tetraoxide for periods varying from 2 to 5 minutes. The samples were then rinsed in sterile water followed by immersion in a phosphate buffered saline solution which contained polyvinylpyrrolidone.

The samples were then cut into 50 pieces and incubated individually in 50 separate test tubes (20×150 mm) into which 17 ml of Qmod growth medium had been added. After one week, 28 of the test tubes were observed to contain pure cultures of a Frankia strain isolate, indicating a 56% success rate.

While the processes and compositions herein described constitute preferred embodiments of the invention, it is to be understood that the invention is not limited to these precise processes and compositions, and that changes may be made therein without departing from the scope of the invention.

What is claimed is:

1. A process for isolating symbiotic microorganisms from host plants comprising the steps of:
   (a) contacting root tissue taken from said host plants with an aqueous solution of osmium tetraoxide for a time sufficient to effect sterilization of the surface and subsurface area of said root tissue but insufficient to kill all of said symbiotic microorganisms,
   (b) rinsing said root tissue to remove osmium tetraoxide and to terminate the progress of sterilization,
   (c) dividing said root tissue into a plurality of samples containing said symbiotic microorganisms, and
   (d) transferring said samples to a growth medium to provide a pure culture of said symbiotic microorganisms.

2. The process of claim 1 in which said osmium tetraoxide is present in said solution at a concentration of from 1-5% by weight.

3. The process of claim 1 in which said root tissue is contacted in step (a) for from 30 seconds to 6 minutes.

4. The process of claim 1 in which said symbiotic microorganisms are nitrogen-fixing soil actinomycetes bacteria.

5. The process of claim 1 in which said symbiotic microorganisms are nitrogen-fixing Rhizobium bacteria.

6. The process of claim 1 in which said symbiotic microorganisms are phosphorus-providing endomycorrhizal fungi.

7. The process of claim 1 in which said symbiotic microorganisms are phosphorus-providing ectomycorrhizal fungi.

* * * * *